United States Patent
Akita et al.

(10) Patent No.: US 7,484,849 B2
(45) Date of Patent: Feb. 3, 2009

(54) OPHTHALMOLOGIC OBSERVATION APPARATUS

(75) Inventors: Junichi Akita, Nukata-gun (JP); Akihiro Fujishiro, Toyohashi (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 11/902,926

(22) Filed: Sep. 26, 2007

(65) Prior Publication Data

US 2008/0079900 A1   Apr. 3, 2008

(30) Foreign Application Priority Data

Sep. 29, 2006  (JP)  ............................. 2006-266785

(51) Int. Cl.
*A61B 3/14* (2006.01)
*A61B 3/10* (2006.01)

(52) U.S. Cl. .................. 351/206; 351/208; 351/215

(58) Field of Classification Search ............... 351/205, 351/206–215
See application file for complete search history.

(56) References Cited

U.S. PATENT DOCUMENTS

| | | | |
|---|---|---|---|
| 4,765,730 A | 8/1988 | Webb | 351/205 |
| 5,177,511 A * | 1/1993 | Feuerstein et al. | 351/205 |
| 5,537,163 A * | 7/1996 | Ueno | 351/206 |
| 5,847,805 A * | 12/1998 | Kohayakawa et al. | 351/210 |
| 2005/0231685 A1 | 10/2005 | Akita et al. | 351/215 |

FOREIGN PATENT DOCUMENTS

| | | |
|---|---|---|
| JP | A 62-117524 | 5/1987 |
| JP | A 2005-279121 | 10/2005 |

* cited by examiner

*Primary Examiner*—Mohammed Hasan
(74) *Attorney, Agent, or Firm*—Oliff & Berridge, PLC

(57) ABSTRACT

An ophthalmologic observation apparatus of a confocal laser scanning microscopy system for photographing and observing a target site of an eye of an examinee, includes a controller that, based on a number of image lines of one frame of a motion image to be displayed, a number of reflection faces of a polygon mirror, and a detection result of a photo sensor, controls a galvano mirror and an image forming unit so as to form each image line of each frame of the motion image based on the photo-receiving signals of a laser beam reflected on same reflection face of the polygon mirror.

3 Claims, 3 Drawing Sheets

US 7,484,849 B2

OPHTHALMOLOGIC OBSERVATION APPARATUS

BACKGROUND OF THE INVENTION (1) Technical Field

The present invention relates to an ophthalmologic observation apparatus of a confocal laser scanning microscopy system, for photographing and observing a target site of an eye of an examinee.

(2) Related Art

There is an apparatus for scanning (movably irradiating) a laser beam in a two-dimensional manner to a target site such as a fundus of an examinee, and then, receiving the laser beam reflected at the target site by a photoreceptor element via a pin hole disposed at a position conjugate to the target site, thereby obtaining an image of the target site. In addition, there is an apparatus using a polygon mirror and a galvano mirror in order to scan a laser beam in a two dimensional manner. (Refer to US2005/0231685 A1 (Jap. Pat. Appln. No. KOKAI 2005-279121).)

It is preferable that all of the figure tolerance of each reflection faces of the polygon mirror and an angle between the reflection faces be equal to each other. However, in practice, a manufacture error exist, which lowers an image quality of the image of the target site obtained.

SUMMARY OF THE INVENTION

It is a technical object of the present invention to provide an ophthalmologic observation apparatus capable of obtaining a good image of a target site of a eye of an examinee.

In order to achieve the object described above, the present invention is characterized by having the following configuration.

(1) An ophthalmologic observation apparatus of a confocal laser scanning microscopy system for photographing and observing a target site of an eye of an examinee, the apparatus comprising:

a laser source that emits a laser beam for a predetermined time in order to obtain a motion image of the target site;

a polygon mirror that rotates for a predetermined time at a predetermined speed, reflects the laser beam and scans in a first direction;

a galvano mirror that moves for a predetermined time at a predetermined speed, reflects the laser beam and scans in a second direction orthogonal to the first direction;

a photoreceptor element that receives the laser beam reflected at the target site;

an image forming unit that forms the motion image of the target site based on photo-receiving signals of the photoreceptor element;

a display unit that displays the formed motion image;

a light source that emits to the polygon mirror, detecting light of a wavelength that is different from a wavelength of the laser beam;

a photo sensor that receives the detecting light reflected by the polygon mirror; and a controller that, based on the number of image lines of one frame of the motion image to be displayed, the number of reflection faces of the polygon mirror, and a detection result of the photo sensor, controls the galvano mirror and the image forming unit so as to form each image line of each frame of the motion image based on the photo-receiving signals of the laser beam reflected on same reflection face of the polygon mirror.

(2) The ophthalmologic observation apparatus according to (1), wherein the number of the image lines of one frame of the motion image is a multiple of the number of the reflection faces of the polygon mirror.

(3) The ophthalmologic observation apparatus according to (1), further comprising:

a first filter disposed in front of the photoreceptor element and having a feature of transmitting the laser beam and interrupting the detecting light; and a second filter disposed in front of the photo sensor and having a feature of transmitting the detecting light and interrupting the laser beam.

DESCRIPTION OF PREFERRED EMBODIMENT(S)

Figure 1:
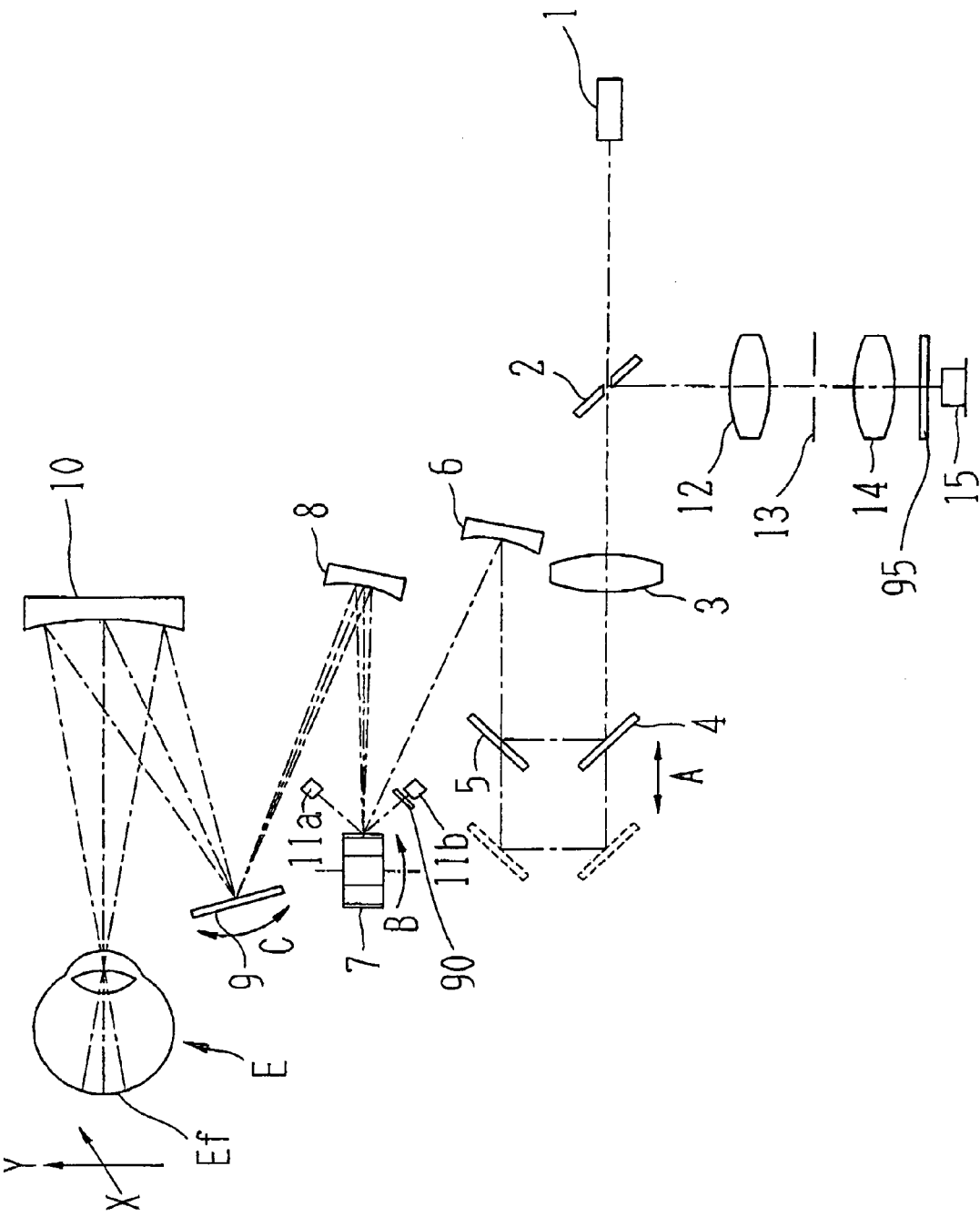
FIG. 1 is a schematic view of an optical system of an ophthalmologic observation apparatus according to an embodiment of the present invention.

A preferred embodiment of the present invention will be described with reference to the accompanying drawings. FIG. 1 is a schematic view of an optical system of an ophthalmologic observation apparatus according to an embodiment of the present invention.

A laser beam emitted from a laser source 1 passes through a substantially central opening of a hole mirror 2, and then, the laser beam transmits a lens 3. Then, the laser beam is reflected on planer mirrors 4 and 5 and a concave mirror 6, and then, the laser beam is incident to a polygon mirror 7. The laser beam reflected on the polygon mirror 7 is reflected on a concave mirror 8, and then, the laser beam is incident to a galvano mirror 9. The laser beam reflected on the galvano mirror 9 is reflected on a concave mirror 10, and then, the laser beam focuses at a target site of a fundus Ef of an eye E of an examinee. The mirrors 4 and 5 are movably disposed in the direction indicated by an arrow A in FIG. 1, and then, an optical path length of the laser beam is changed by being moved, whereby focus adjustment (diopter movement) is effected. The polygon mirror 7 is a scanning unit for scanning (movably irradiating) the laser beam in a horizontal direction (X-axis direction), and is rotated at a predetermined speed in one-directional manner (direction indicated by an arrow B in FIG. 1) of the horizontal direction. The galvano mirror 9 is a scanning unit for scanning (movably irradiating) the laser beam in a vertical direction (Y-axis direction orthogonal to the X-axis direction), and is swung (rotated) at a predetermined speed in a bi-directional manner (direction indicated by an arrow C in FIG. 1) of the vertical direction. In other words, a scanning (irradiation) optical system of the laser beam is comprised of these optical members. In the present embodiment, a semiconductor laser that emits an infrared laser beam having a wavelength of 790 nm is employed for the laser source 1.

The laser beam reflected at the target site travels backward to the scanning optical system described above, and then, the laser beam is reflected on an opening peripheral face of the hole mirror 2. Then, the laser beam transmits a lens 12, and then, the laser beam forms a focal point at a pin hole of a pin hole plate 13. Then, the laser beam transmits a lens 14 and a filter 95, and then, the laser beam is received by a photoreceptor element 15. The opening of the hole mirror 2 is disposed at a position that is substantially conjugate to a pupil of the eye E on an optical axis of the scanning optical system (photoreceptor optical system). The pin hole of the pin hole plate 13 is disposed at a position that is substantially conjugate to the target site of the fundus Ef on the optical axis of the photoreceptor optical system. The filter 95 is disposed immediately in front of the photoreceptor element 15, and has a feature of transmitting the laser beam and interrupt lights other than the laser beam. In other words, the photoreceptor (photography) optical system of the laser beam is comprised of these optical members. In the present embodiment, an avalanche photodiode is employed for the photoreceptor element 15.

Figure 2:
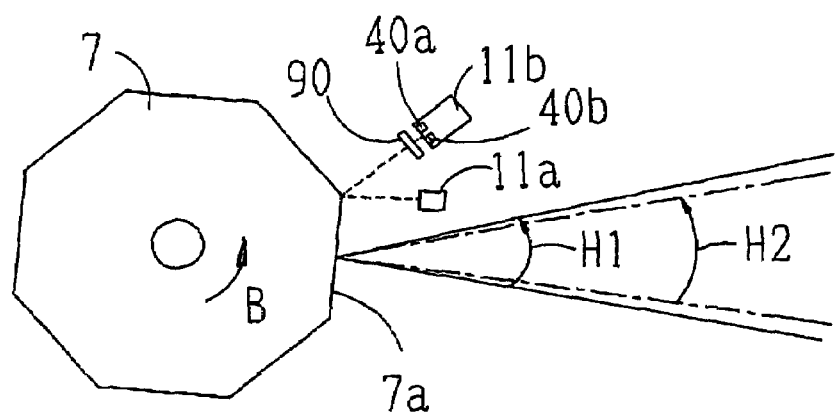
FIG. 2 is a schematic view of an optical system for detecting switching of a reflection face of a polygon mirror.

Detecting light emitted from a light source 11a that emits light having a wavelength that is different from that of the laser beam is incident to the polygon mirror 7 in order to detect switching of a reflection face of the polygon mirror 7 to which the laser beam from the laser source 1 is incident. The detecting light reflected on the polygon mirror 7 transmits a filter 90, and then, the detecting light is received (detected) by a photo sensor 11b. In FIG. 2, a range H1 indicates a scanning range of the laser beam by reflection on a certain reflection face 7a due to rotation of the polygon mirror 7. In addition, a range H2 indicates a scanning range of the laser beam employed for forming an image in the range H1. The light source 11a and the photo sensor 11b are disposed so that start of scanning of the laser beam by reflection on each reflection face of the polygon mirror 7 can be detected every time when the reflection face is switched. In addition, the light source 11a and the photo sensor 11b are vertically divided with a rotational face of the polygon mirror 7 as being a boundary, and then, they are disposed out of the scanning range of the laser beam (refer to FIG. 1). The filter 90 is disposed immediately in front of the photo sensor 11b, and has a feature of transmitting the detecting light and interrupting lights other than the detecting light. In other words, a detecting optical system for detecting switching of the reflection face of the polygon mirror 7 is comprised of these optical members. In the present embodiment, a light emitting diode that emits infrared light having a wavelength of 950 nm is employed for the light source 11a.

In addition, in the present embodiment, two photoreceptor elements 40a and 40b are provided at the photo sensor 11b in parallel to a rotational direction of the polygon mirror 7, so that the detecting light from the light source 11a is received at a timing different from another one (refer to FIG. 2). In this case, waveforms of photo-receiving signals outputted from the photoreceptor elements 40a and 40b are identical to each other, but the timings to be outputted are different from each other. Therefore, noise can be reduced by obtaining a sync signal based on a time at which the waveforms of the photo-receiving signals from the photoreceptor elements 40a and 40b (a time at which outputs are equal to each other).

Figure 3:
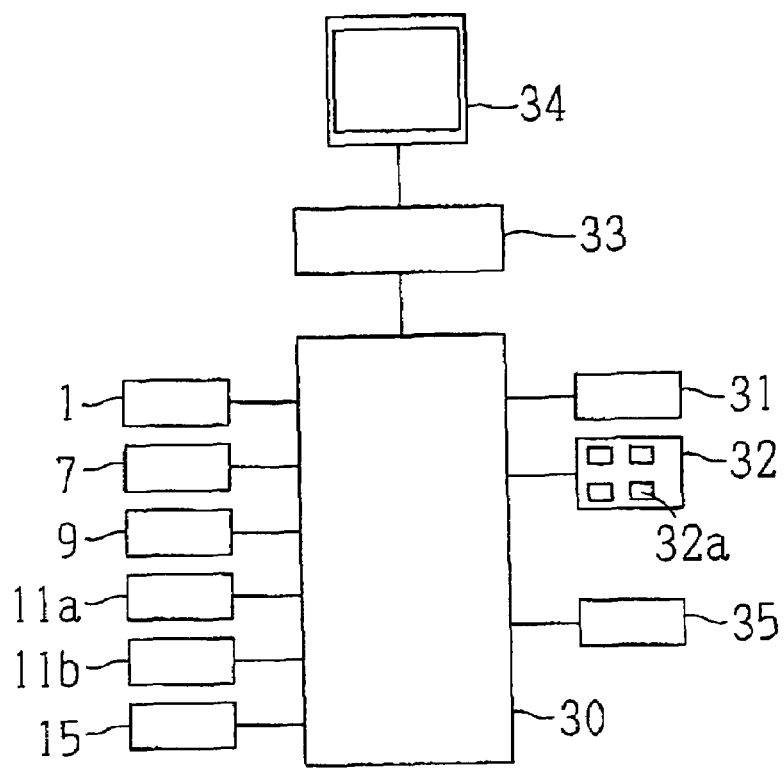
FIG. 3 is a schematic block diagram of a control system of the apparatus.

FIG. 3 is a schematic block diagram of a control system of this apparatus.

Constituent elements such as the laser source 1, the polygon mirror 7, the galvano mirror 9, the light source 11a, the photo sensor 11b, the photoreceptor element 15, moving units 31 of the mirrors 4 and 5, an input unit 32, an image forming unit 33, a monitor (display unit) 34, and a memory (storage unit) 35, are connected to a controller (control unit) 30 that controls the entire apparatus.

An operation of the apparatus having the constituent elements described above will be described here.

When refractive power of the eye E measured in advance by an equipment such as an eye refractive power measuring apparatus is inputted by operation of the input portion 32, the controller 30 stores the inputted refractive power in the memory 35 and moves the mirrors 4 and 5 by the moving unit 31. Next, by a manual alignment mechanism and/or automatic alignment mechanism (not shown), alignment of the apparatus (optical system) is carried out so that the laser beam focuses at the target site of the fundus Ef. In addition, output power of the laser beam is adjusted by operation of an output adjustment button 32a of the input unit 32.

The laser beam from the laser source 1 is reflected on the rotating polygon mirror 7, and the reflected laser beam is scanned in the horizontal direction. The laser beam scanned by the polygon mirror 7 is reflected on the swinging galvano mirror 9, and the reflected laser beam is scanned in a vertical direction. In other words, the laser beam is scanned in a two-dimensional manner by the polygon mirror 7 and the galvano mirror 9. The laser beam reflected at the target site is received by the photoreceptor element 15.

In the present embodiment, the light source 11a and the photo sensor 11b are disposed so that the detecting light from the light source 11a is received by the photo sensor 11b at each timing when scanning of the laser beam is started by reflection on each reflection face of the polygon mirror 7. In addition, the scanning optical system, the photoreceptor optical system and the detecting optical system are set, and image forming is controlled, so that photo-receiving signals from a first predetermined time succeeding, to a second determined time succeeding to the time when a photo-receiving signal is sent from the photo sensor 11b, is defined as photo-receiving signals of the scanning range H2, from among the photo-receiving signals in the scanning range H1 sent from the photoreceptor element 15.

Figure 4:
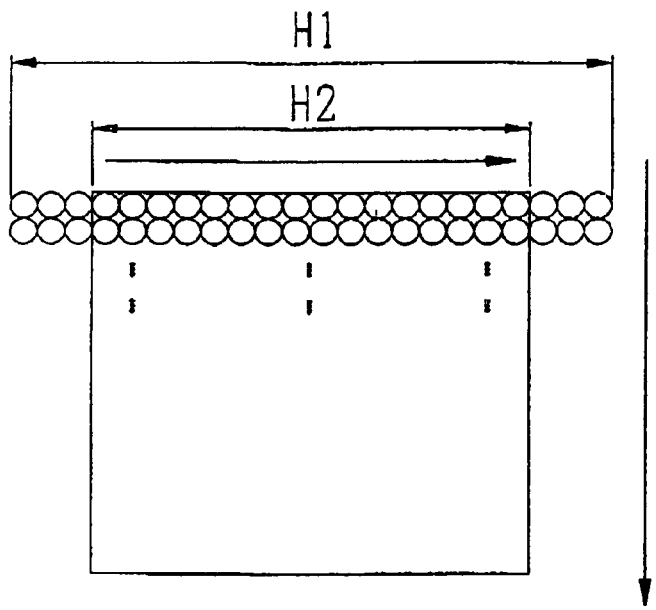
FIG. 4 is an explanatory view of image forming.

When the laser beam is reflected on a certain reflection face by rotation of the polygon mirror 7, and then, a photo-receiving signal is sent from the photo sensor 11b, the controller 30 sends to the image forming unit 33 only photo-receiving signals of the scanning range H2 from among photo-receiving signals of the scanning range H1 sent from the photoreceptor element 15. The image forming unit 33, as shown in FIG. 4, arranges the photo-receiving signals of the scanning range H2 from the photoreceptor element 15 as image data in sequential order in a transverse direction. Then, the image forming unit 33 forms a first image line (scanning line).

When the laser beam is reflected on a next reflection face by further rotation of the polygon mirror 7, and a photo-receiving signal is sent from the photo sensor 11b again, the controller 30 sends to the image forming unit 33 only photo-receiving signals of the scanning range H2 sent from the photoreceptor element 15. The image forming unit 33, as shown in FIG. 4, arranges the photo-receiving signals of the scanning range H2 from the photoreceptor element 15 as image data in sequential order in the transverse direction one stage below the preceding image line. Then, the image forming unit 33 forms a next image line (scanning line).

The controller 30 and the image forming unit 33 form image lines of one frame of a motion image in number stored in advance in the memory 25. In addition, the controller 30 sequentially counts photo-receiving signals sent from the photo sensor 11b. When the photo-receiving signals in number of the image lines of one frame of the motion image stored in advance in the memory 35 are obtained, the controller resets the reflection angle of the galvano mirror 9 up to the reflection angle at the time of start of scanning so that next one frame of the motion image is formed.

By such image forming control, even if an angle between the reflection faces of the polygon mirror 7 has an error, a good motion image of the target site can be displayed.

In addition, the wavelength of the laser beam for forming the image of the target site is different from that of the detecting light, the filter 95 having the feature described above is disposed in front of the photoreceptor element 15 for receiving the laser beam, and the filter 90 having the feature described above is disposed in front of the photo sensor 11b for receiving the detecting light. Thus, noise occurred by a scattering light generated by the reflection face of the polygon mirror 7 can be reduced.

In addition, in the case of obtaining the motion image of the target site, the controller 30 controls the galvano mirror 9 and the image forming unit 33 so as to always form each image line of each frame of the motion image, based on photo-receiving signals of the laser beam reflected on the same reflection face of the polygon mirror 7.

Figure 5:
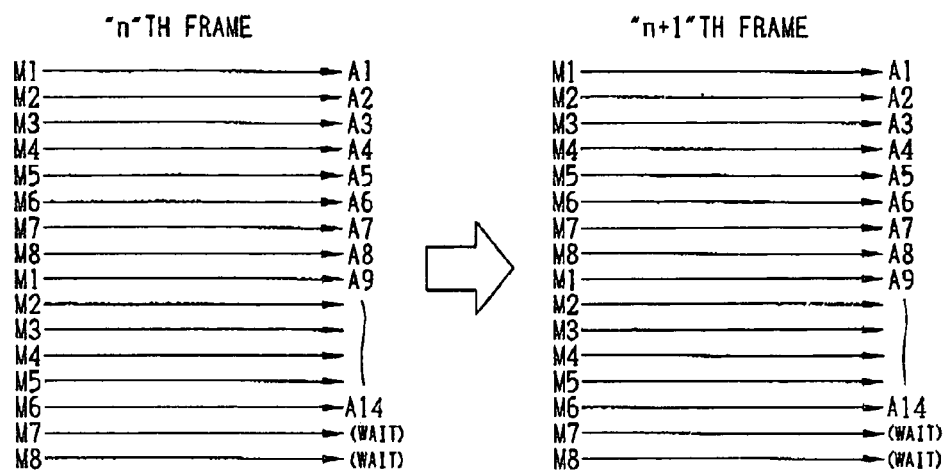
FIG. 5 is an explanatory view of image forming.

Such image forming control will be described with reference to FIG. 5. The controller 30 defines a reflection face of the polygon mirror 7 for each image line, based on the number of the image lines of one frame of the motion image and the number of the reflection faces of the polygon mirror 7, stored in advance in the memory 25. For example, in the case where the number of the reflection faces of the polygon mirror 7 is 8 (reflection faces M1 to M8) and the number of the image lines of one frame of the motion image is 14 (image lines A1 to A14), reflection faces are allocated to image lines so that a reflection face M1 (reflection face corresponding to a first photo-receiving signal of the photo sensor 11b) is used for a first image line A1; a next reflection face M2 (reflection face corresponding to a second photo-receiving signal of the photo sensor 11b) is used for a second image line A2; a reflection face M8 (reflection face corresponding to a eighth photo-receiving signal of the photo sensor 11b) is used for a eighth image line A8; the reflection face M1 (reflection face corresponding to a ninth photo-receiving signal of the photo sensor 11b) is used again for a ninth image line A9; the reflection face M2 (reflection face corresponding to a tenth photo-receiving signal of the photo sensor 11b) is used for a tenth image line A10; and a reflection face M6 (reflection face corresponding to a 14th photo-receiving signal of the photo sensor 11b) is used for a last image line A14.

The controller 30 can specify a reflection face of the polygon mirror 7 as described above, based on sequential order of photo-receiving signals sequentially sent from the photo sensor 11b. Therefore, when next one frame is formed after one frame of the motion image has been formed, the controller 30 controls the galvano mirror 9 and the image forming unit 33 to cause them to wait for image forming of the image line A1 until the photo-receiving signal corresponding to the reflection face M1 for the image line A1 is sent from the photo sensor 11b; and then, starts image forming of the image line A1 when the photo-receiving signal corresponding to the reflection face M1 for the image line A1 is sent from the photo sensor 11b.

By such image forming control, each image line of each frame of the motion image is always formed based on the photo-receiving signals of the laser beam reflected on the same reflection face of the polygon mirror 7, so that, even if the figure tolerance of the reflection faces of the polygon mirror 7 has an error, a good motion image of the target site can be displayed. If the figure tolerance of the reflection faces of the polygon mirror 7 has an error and each image line of each frame of the motion image are not always formed based on the photo-receiving signals of the laser beam reflected on the same reflection face, the motion image is displayed so that the light and dark portions which are different on a frame by frame basis of the motion image move vertically. (A so called "flowing noise" is observed).

As long as the number of the image lines of one frame of the motion image is a multiple of the number of the reflection faces of the polygon mirror 7, image forming control is facilitated. For example, in the case where the number of the reflection faces of the polygon mirror 7 is 8 (reflection faces M1 to M8) and the number of the image lines of one frame of the motion image is 16 (image lines A1 to A16), reflection faces are allocated to image lines so that a reflection face M1 (reflection face corresponding to a first photo-receiving signal of the photo sensor 11b) is used for a first image line A1; a reflection face M8 (reflection face corresponding to a eighth photo-receiving signal of the photo sensor 11b) is used for a eighth image line A8; the reflection face M1 (reflection face corresponding to a ninth photo-receiving signal of the photo sensor 11b) is used again for a ninth image line A9; and the reflection face M8 (reflection face corresponding to a 16th photo-receiving signal of the photo sensor 11b) is used for a last image line A16. In addition, when next one frame is formed, reflection faces are allocated to image lines in the same manner as when previous one frame has been formed.

Further, the target site may be a portion such as an anterior ocular segment without being limitative to the fundus.

What is claimed is:

1. An ophthalmologic observation apparatus of a confocal laser scanning microscopy system for photographing and observing a target site of an eye of an examinee, the apparatus comprising:

a laser source that emits a laser beam for a predetermined time in order to obtain a motion image of the target site;

a polygon mirror that rotates for a predetermined time at a predetermined speed, reflects the laser beam and scans in a first direction;

a galvano mirror that moves for a predetermined time at a predetermined speed, reflects the laser beam and scans in a second direction orthogonal to the first direction;

a photoreceptor element that receives the laser beam reflected at the target site;

an image forming unit that forms the motion image of the target site based on photo-receiving signals of the photo receptor element;

a display unit that displays the formed motion image;

a light source that emits to the polygon mirror, detecting light of a wavelength that is different from a wavelength of the laser beam;

a photo sensor that receives the detecting light reflected by the polygon mirror; and a controller that, based on the number of image lines of one frame of the motion image to be displayed, the number of reflection faces of the polygon mirror, and a detection result of the photo sensor, controls the galvano mirror and the image forming unit so as to form each image line of each frame of the motion image based on the photo-receiving signals of the laser beam reflected on same reflection face of the polygon mirror.

2. The ophthalmologic observation apparatus according to claim 1, wherein the number of the image lines of one frame of the motion image is a multiple of the number of the reflection faces of the polygon mirror.

3. The ophthalmologic observation apparatus according to claim 1, further comprising:
- a first filter disposed in front of the photoreceptor element and having a feature of transmitting the laser beam and interrupting the detecting light; and
- a second filter disposed in front of the photo sensor and having a feature of transmitting the detecting light and interrupting the laser beam.

* * * * *